United States Patent [19]

Kasuga et al.

[11] Patent Number: 4,960,733
[45] Date of Patent: Oct. 2, 1990

[54] INORGANIC BIOMATERIAL AND PROCESS FOR PRODUCING THE SAME

[75] Inventors: Toshihiro Kasuga; Masahiro Yoshida; Tomoko Uno, all of Akishima; Kiichi Nakajima, Kokubunji, all of Japan

[73] Assignee: Hoya Corporation, Tokyo, Japan

[21] Appl. No.: 159,606

[22] Filed: Feb. 24, 1988

[30] Foreign Application Priority Data

Feb. 28, 1987 [JP] Japan .................................. 62-46476
Nov. 30, 1987 [JP] Japan .................................. 62-302817

[51] Int. Cl.$^5$ ...................... C03C 10/12; C03C 10/04; C03C 10/06; C03C 10/08
[52] U.S. Cl. ............................................ 501/10; 501/3; 501/5; 501/8; 501/9; 501/32
[58] Field of Search ........................ 501/10, 5, 3, 8, 9, 501/32

[56] References Cited

U.S. PATENT DOCUMENTS

| | | | |
|---|---|---|---|
| 4,560,666 | 12/1985 | Yoshida et al. | 501/10 |
| 4,643,982 | 2/1987 | Kasuga et al. | 501/10 |
| 4,652,534 | 3/1987 | Kasuga | 501/10 |
| 4,783,429 | 11/1988 | Shibuya et al. | 501/10 |
| 4,820,660 | 4/1989 | Mohri et al. | 501/10 |

*Primary Examiner*—Mark L. Bell
*Attorney, Agent, or Firm*—Nixon & Vanderhye

[57] ABSTRACT

The inorganic biomaterial of the present invention comprises a ceramic-crystallized glass composite wherein a zirconia ceramic, an alumina ceramic or a zirconia-alumina ceramic is dispersed in a crystallized glass composed mainly of CaO, $P_2O_5$, MgO and $Al_2O_3$. This inorganic biomaterial, having biocompatibility and a high strength, is useful as an implant material for artificial bones and dental implants.

2 Claims, 3 Drawing Sheets

INORGANIC BIOMATERIAL AND PROCESS FOR PRODUCING THE SAME

BACKGROUND OF THE INVENTION

1. Field of the Invention

The present invention relates to an inorganic biomaterial which is useful as an implant material for artificial bones, dental implants, etc., as well as to a process for producing said inorganic biomaterial.

2. Description of Prior Art

As so-called bioactive ceramics capable of forming a chemical bonding with bones, there are known sintered apatite and a crystallized glass of $Na_2O-K_2O-MgO-CaO-SiO_2-P_2O_5$ type. As the bioactive ceramic, there is further known a crystallized glass obtained by grinding a $MgO-CaO-P_2O_5-SiO_2$ type glass to a particle size of larger (finer) than 200 meshes, molding the resulting glass powder into a desired shape, heat-treating the resulting molding at a temperature range in which the glass powder is sintered, and then heat-treating the resulting sintered product at a temperature range in which an apatite crystal $[Ca_{10}(PO_4)_6(O_{0.5}, F)_2]$ and a wollastonite crystal $[CaSiO_3]$ are precipitated [Japanese Patent Application (Laid-Open) No. 191252/1982]. In this crystallized glass, the apatite crystal contributes to the biocompatibility and the wollastonite crystal contributes to the mechanical strength. Hence, to increase the mechanical strength of the crystallized glass, it is desirable to increase the content of the wollastonite crystal. In this connection, there is furthermore known a crystallized glass obtained by increasing the $SiO_2$ content to form a larger amount of the wollastonite crystal precipitated.

As to the bending strength, the sintered apatite has about 1,000 to 1,400 kg/cm$^2$; the $Na_2O-K_2O-MgO-CaO-SiO_2-P_2O_5$ type crystallized glass about 1,000 to 1,500 kg/cm$^2$; the $MgO-CaO-P_2O_5-SiO_2$ type crystallized glass about 1,200 to 1,400 kg/cm$^2$. The $CaO-P_2O_5-SiO_2$ type or $CaO-P_2O_5-SiO_2-(MgO, Y_2O_3)$ type crystallized glass containing a larger amount of the wollastonite crystal has a high bending strength of 1,700 to 2,300 kg/cm$^2$. However, these values are not yet fully satisfactory from the standpoint that the above materials are used in applications such as artificial bones and dental implants. Hence, a material of higher strength is desired.

Accordingly, an object of the present invention is to provide an inorganic biomaterial having excellent biocompatibility and a higher strength than conventional biomaterials, as well as to a process for producing said biomaterial.

Other objects of the present invention will become apparent from the following description and the accompanying drawings.

SUMMARY OF THE INVENTION

The inorganic biomaterial of the present invention achieving the above objects consists of a ceramic-crystallized glass composite wherein a zirconia alumina ceramic is dispersed in a crystallized glass comprising the following components of the following proportions

| | |
|---|---|
| CaO | 12 to 56% by weight |
| $P_2O_5$ | 1 to 27% by weight |
| $SiO_2$ | 22 to 50% by weight |
| MgO | 0 to 34% by weight |
| $Al_2O_3$ | 0 to 25% by weight | in a total amount of at least 90% by weight.

The inorganic biomaterial as mentioned above can be produced by mixing a matrix glass powder comprising the following components of the following proportions

| | |
|---|---|
| CaO | 12 to 56% by weight |
| $P_2O_5$ | 1 to 27% by weight |
| $SiO_2$ | 22 to 50% by weight |
| MgO | 0 to 34% by weight |
| $Al_2O_3$ | 0 to 25% by weight | in a total amount of at least 90% by weight, with a zirconia-alumina ceramic powder, molding the resulting mixture into a desired shape, and heat-treating the resulting molding to sinter it and to uniformly precipitate in the glass, a crystal of apatite and at least one crystal of an alkaline earth metal silicate selected from the group consisting of wollastonite, diopside, forsterite, akermanite and anorthite.

DETAILED DESCRIPTION OF THE INVENTION

Figure 1:
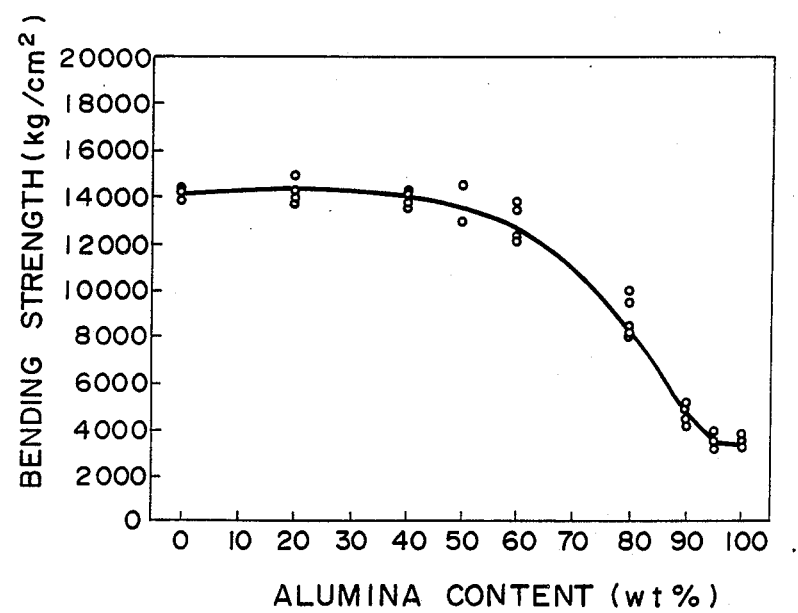
FIG. 1 is a graph showing the relationship between alumina content (wt. %) in zirconia-alumina ceramic and bending strength, of an inorganic biomaterial consisting of a zirconia-alumina ceramic/crystallized glass composite, obtained according to the present invention.

The inorganic biomaterial of the present invention comprises a crystallized glass as a matrix. The crystallized glass comprises an apatite crystal, at least one crystal of an alkaline earth metal silicate selected from the group consisting of wollastonite, diopside, forsterite, akermanite, anorthite, etc., and further in some cases, beta type tricalcium phosphate crystal [$\beta$-$Ca_3(PO_4)_2$].

In the inorganic biomaterial of the present invention, the amounts of the components in the matrix glass are restricted as mentioned above. The reason is described below.

When the CaO content is less than 12%, the glass powder has very poor sinterability making it difficult to obtain a crystallized glass of high strength. When the content is more than 56%, the resulting glass has a high tendency of devitrification. Accordingly, the CaO content is restricted to fall within a range of 12 to 56%. When the $P_2O_5$ content is less than 1%, the resulting glass has a high tendency of devitrification. When the content is more than 27%, the total amount of the precipitated crystals of alkaline earth metal silicates such as wollastonite, diopside, forsterite, akermanite, anorthite and the like is small. Therefore, the $P_2O_5$ content is restricted to 1%–27%. When the $SiO_2$ content is less than 22%, the glass powder has poor sinterability and the total amount of the precipitated crystals of alkaline earth metal silicates is small. When the content is more than 50%, the resulting glass tends to be devitrified. Hence, the $SiO_2$ content is restricted to 22%–50%. MgO is not an essential component but when it is contained, an apatite crystal is formed in too small an amount, if the content is more than 34%. Therefore, the MgO content is restricted to 34% or below. $Al_2O_3$ is not an essential component, either. However, when it is contained, an apatite crystal is formed in too small an amount, if the content is more than 25%. Therefore, the $Al_2O_3$ content is restricted to 25% or below. The total content of the above five components, i.e., CaO, $P_2O_5$, $SiO_2$, MgO and $Al_2O_3$ is at least 90% for the reasons described below.

In the present invention, the matrix glass can comprise, in addition to the above five components, at least one component selected from $K_2O$, $Li_2O$, $Na_2O$, $TiO_2$, $ZrO_2$, SrO, $Nb_2O_5$, $Ta_2O_5$, $B_2O_3$, $F_2$ and $Y_2O_3$ all of which give no harm to human bodies) in a predetermined amount. When the total content of these optional components is more than 10%, the amounts of apatite crystal and alakaline earth metal silicate crystal(s) formed decrease in some cases. Therefore, the content of the above optional components is restricted at below 10%. When the $F_2$ content is more than 5%, the resulting glass is easily devitrified. When the $Y_2O_3$ content is more than 5%, the amounts of apatite crystal and alkaline earth metal silicate crystal(s) formed decrease. Accordingly, the $F_2$ content and the $Y_2O_3$ content are each restricted to 5% or below.

In the inorganic biomaterial of the present invention, the zirconia-alumina ceramic to be dispersed in the matrix glass is obtained by reinforcing alumina by utilizing (a) the stress-induced transformation (martensitic transformation) of the tetragonal zirconia particles ordinarily containing a small amount of $Y_2O_3$, CaO, MgO, $CeO_2$, etc. or (b) microcrack-toughening and accordingly has a very high strength and a very high toughness. The weight ratio of zirconia to alumina in the zirconia-alumina ceramic is preferably 99.7:0.3 to 10:90. A zirconia-alumina ceramic of higher strength and higher toughness can be obtained when the zirconia content is higher than the alumina content. For example, by mixing a tetragonal zirconia containing 2 mole % of $Y_2O_3$ with an alpha-alumina at a weight ratio of 80:20 and sintering the mixture at 1,500° C. according to the hot isostatic pressing method, there can be obtained a high strength and high toughness ceramic having a bending strength of 20,000 to 24,000 kg/cm$^2$ and a fracture toughness $K_{IC}$ of 10 MNm$^{-\frac{3}{2}}$. Also when in the above procedure the weight ratio of the tetragonal zirconia to the alpha-alumina is 60:40, the resulting ceramic shows similar mechanical properties. The inorganic biomaterial of the present invention uses such a zirconia-alumina ceramic as a reinforcing agent and thereby has a high strength. The addition of such a small amount of alumina as 0.3–5% by weight contributes to the increase in the density of the sintered product.

The reason for the high strength of the inorganic biomaterial of the present invention due to the use of the zirconia-alumina ceramic is that when the inorganic biomaterial is destroyed, main cracks must change the directions of their progress when they hit zirconia-alumina particles of high strength and high toughness dispersed in the crystallized glass and therefore a large energy is required for the inorganic biomaterial to be destroyed.

In producing an inorganic biomaterial of the present invention, a matrix glass having a composition as specified above is ground to a particle size of preferably larger (finer) than 200 meshes and then uniformly mixed with a zirconia-alumina ceramic according to any known method. The reason for the particle size of preferably larger (finer) than 200 meshes is as follows. When the matrix glass has a particle size of smaller (coarser) than 200 meshes, the sintered product resulting from the above mixture tends to have remaining pores, making it difficult to obtain a ceramic-crystallized glass composite of high mechanical strength. In contrast, when the matrix glass has a particle size of larger (finer) than 200 meshes, the resulting sintered product has less pores, making it possible to obtain a ceramic-crystallized glass composite wherein the crystals are formed uniformly and the zirconia-alumina ceramic particles are distributed uniformly. Therefore, use of a matrix glass powder having a particle size of larger (finer) than 200 meshes is necessary to obtain a ceramic-crystallized glass composite wherein only a small number of pores remain, the crystals are formed uniformly and the zirconia-alumina ceramic particles are distributed uniformly.

Similarly, the zirconia-alumina ceramic to be mixed with the matrix glass is also preferred to have a particle size of larger (finer) than 200 meshes. The reason is that when the zirconia-alumina ceramic powder has a particle size of larger (finer) than 200 meshes, the sintered product obtained has no pores, making it possible to produce a ceramic-crystallized glass composite of high mechanical strength. Therefore, use of a glass powder having a particle size of larger (finer) than 200 meshes and a zirconia-alumina ceramic powder having a particle size of larger (finer) than 200 meshes is necessary to obtain a ceramic-crystallized glass composite wherein only a small number of pores remain and the crystals are distributed uniformly.

The mixing ratio of the matrix glass powder and the zirconia-alumina ceramic powder is preferred to be 95:5 to 5:95 by volume. The reason is that this range enables production of an inorganic biomaterial of high bending strength without secrifying the bioactivity.

The thus obtained mixture of the glass powder and the zirconia-alumina ceramic powder is molded into a desired shape by a known molding method such as die molding, cast molding, injection molding, rubber press molding or the like. Then, the resulting molding i heat-treated within the sintering temperature range and further heat-treated within the temperature ranges in which an apatite crystal and at least one crystal of an alkaline earth metal silicate are precipitated. The former heat treatment is necessary to obtain a ceramic-crystallized glass composite having only a small number of pores and a high mechanical strength and the latter heat treatment is necessary to precipitate in the glass an apatite crystal and at least one crystal of an alkaline earth metal silicate.

The sintering temperature range can be determined by heating the molding of the mixture of the matrix glass powder and the zirconia-alumina ceramic powder at a constant rate and measuring the thermal contraction during the heating. The temperature range from the start of the thermal contraction to its completion is the sintering temperature range of the molding.

The temperature ranges in which an apatite crystal and at least one crystal of an alkaline earth metal silicate are precipitated can be obtained from the differential thermal analysis of the glass/zirconia-alumina ceramic mixture. That is, the glass/zirconia-alumina ceramic mixture is subjected to differential thermal analysis to obtain an exothermic peak; separately, the mixture is heat-treated at each exothermic peak temperature of the differential thermal analysis curve obtained above and then subjected to X-ray diffraction method, and the resulting data are analyzed to identify each crystal precipitated during each of the above heat treatments; and each temperature range from the start of heat generation to its completion in the above differential thermal analysis is taken as the temperature range in which each crystal is precipitated.

The heat treatment of the molding can be conducted according to a known method. The normal pressure calcination may be employed, but the hot pressing method or the hot isostatic pressing (HIP) method is preferred because they give a product of a higher degree of sintering, only a small number of pores and a higher mechanical strength. Of the hot pressing method and the hot isostatic pressing method, the latter is superior because it enables molding into any desired shape including a complex shape.

According to the finding by the present inventors, an inorganic biomaterial having a high strength and a color very close to that of living human bones can be obtained very easily by subjecting the above mentioned molding of the mixture of the glass powder and the zirconia-alumina ceramic powder to preliminary calcination at 650° to 1,500° C. and subjecting the resulting preliminary calcination product to hot isostatic pressing at 900° to 1,500° C. using a pressure medium gas containing oxygen. Ordinarily, the hot isostatic pressing is conducted using a molybdenum or graphite heater and, as a pressure medium, a non-oxidizing gas such as argon, helium or the like; therefore, the inorganic biomaterial obtained contains a small amount of carbon or carbide and accordingly has a black color; when such a black inorganic biomaterial is implanted into a living body, the chemically reduced portions or carbide-containing portions of the biomaterial may have poor biocompatibility, and when used as, for example, a dental implant, the black dental implant is inferior in apperance to natural white teeth. In contrast, the inorganic biomaterial obtained by subjecting the molding firstly to preliminary calcination and then to hot isostatic pressing in an oxygen atmosphere has a color very close to that of living human bones because this two-step heat treatment gives rise to sintering and crystallization. The process for producing an inorganic biomaterial which comprises the two-step heat treatment, i.e., preliminary calcination and hot isostatic pressing in an oxygen atmosphere is described in more detail. The preliminary calcination is conducted at 650° to 1,500° C. as mentioned above. The reason for setting the preliminary calcination temperature at 650° to 1,500° C. is as follows. When the molding is heat-treated at 650° to 1,500° C., the resulting sintered product has a relative density of at least 90% and has no open pores [this can be confirmed by observation by scanning electron microscope (SEM)]. This sintered product, when subjected to hot isostatic pressing, has a relative density of higher than 95% and is very dense. In contrast, when the molding is heat-treated at temperatures lower than 650° C., the resulting product has an insufficient degree of sintering and a relative density of lower than 90%. When the molding Is heat-treated at temperatures hI&her than 1,500° C., the crystallized glass portions of the resulting product melt and form pores or react with the ceramic. The preliminary calcination can be conducted according to any of the normal pressure calcination method and the vacuum calcination method both capable of giving rise to sintering and crystallization, but the vacuum calcination method is superior in that it can provide a preliminary calcination product of higher relative density. Incidentally, in order to obtain a sintered product of high density after hot isostatic pressing, it is desirable that the preliminary calcination product have a relative density as high as possible.

The preliminary calcination product is then subjected to hot isostatic pressing at 900° to 1,500° C. using a pressure medium gas containing oxygen. This hot isostatic pressing under an oxygen-containing atmosphere serves to prevent the resulting product from blackening, thus enabling the production of an inorganic biomaterial having a color very close to that of living human bones.

The oxygen content in the pressure medium gas is preferably 0.2 to 40% by volume, more preferably 0.5 to 20% by volume. When the content is less than 0.2% by volume, the sintered product has slight blackening at the surface. When the content is more than 40% by volume, the operation of the hot isostatic pressing is dangerous.

The reason for setting the temperature of the hot isostatic pressing at 900° to 1,500° C. is as follows. The hot isostatic pressing at 900° to 1,500° C. can allow resulting sintered product to contain sufficient amounts of crystals and thereby to have a sufficiently high strength. In contrast, when the temperature of the high isostatic pressing is lower than 900° C., the amount of the crystals formed is not enough for the resulting sintered product to have a sufficiently high strength. When the temperature of the hot isostatic pressing is higher than 1,500° C., the portions of the crystallized glass in the sintered product melt and form pores or react with the ceramic.

The pressure of the hot isostatic pressing is preferably at least 300 kg/cm$^2$. The reason is that a pressure of at least 300 kg/cm$^2$ allows the remaining of only a small number of pores.

The production of an inorganic biomaterial having a high strength and a color very close to that of living human bones by conducting preliminary calcination and subsequent hot isostatic pressing in an oxygen-containing atmosphere is possible not only when using a zirconia-alumina ceramic but also when using a zirconia ceramic and/or an alumina ceramic. That is, a zirconia ceramic and/or an alumina ceramic is used in place of a zirconia-alumina ceramic; the ceramic(s) is mixed with a matrix glass having a composition as specified previously; the resulting mixture is molded into a desired shape; and the resulting molding is subjected to preliminary calcination at 650° to 1,500° C. and then to hot isostatic pressing at 900° to 1,500° C. using a pressure medium gas containing oxygen, whereby there is obtained an inorganic biomaterial consisting of a ceramic-crystallized glass composite having a high strength and a color very close to that of living human bones. In this case, the operation conditions including the oxygen content in the pressure medium gas and the pressure of the hot isostatic pressing can be same as those used when employing a zirconia-alumina ceramic.

The present invention is explained in more detail below by way of Examples. However, the present invention is in no way restricted to these Examples.

EXAMPLE 1

(PRODUCTION OF ZIRCONIA-ALUMINA CERAMIC/CRYSTALLIZED GLASS COMPOSITE BY USING HOT PRESSING)

Using oxide, carbonate, phosphate, hydrate, fluoride, etc. as raw materials, there was prepared a material batch for a matrix glass having a composition as shown in Table 1. This material batch was placed in a platinum crucible and melted for 2 hours at 1,450° to 1,550° C. The resulting melt was poured into water for quenching. The solid obtained was dried and then ground in a ball mill to a particle size of 20 μm or below (625 meshes or finer). Separately, a powder of tetragonal zirconia and a powder of alpha-alumina were mixed in a ratio (wt. %) as shown in Table 1, and the resulting mixture was calcinated to obtain a zirconia-alumina ceramic powder having a particle size of 300 meshes. This ceramic powder was added to the above obtained matrix glass powder in a proportion (vol. %) as shown in Table 1. They were wet-mixed in a ball mill for several hours and then dried. The resulting mixture was molded in a graphite mold, and the resulting molding was heated at a constant temperature-elevating rate of 3° C./min from room temperature to 1,150° C. while applying a pressure of 300 kg cm² and was kept at 1,150° C. for 2 hours to give rise to sintering and crystallization. Thereafter, the sintered product was cooled to room temperature to obtain a zirconia-alumina ceramic/crystallized glass composite.

On the various ceramic-crystallized glass composites thus obtained, their sections were observed using a scanning electron microscope (SEM). All the sections showed substantially no pores and a dense structure. Further, these composites were ground and, using the resulting powders, the crystalline phases precipitated in the matrix glass were identified according to the method of powder X-rays diffraction. Furthermore, the composites were processed into respective round rods of 3 to 5 mm in diameter using a No. 300 diamond whetstone, and each rod was subjected to three-point bending test. The three-point bending strength of each ceramic-crystallized glass composite is shown in Table 1, together with the glass composition, the zirconia-alumina ceramic composition, the proportion of zirconia-alumina ceramic added (volume % of zirconia-alumina ceramic in a mixture of glass and zirconia-alumina ceramic), and the crystalline phases precipitated in the glass. As is clear from Table 1, all of the inorganic biomaterials of this Example had high bending strengths ranging from 1,800 to 3,800 kg/cm².

EXAMPLE 2

(PRODUCTION OF ZIRCONIA-ALUMINA CERAMIC/CRYSTALLIZED GLASS COMPOSITE BY USING ZIRCONIA-ALUMINA CERAMIC POWDER AND HOT ISOSTATIC PRESSING IN OXYGEN ATMOSPHERE)

Using oxide, carbonate, phosphate, hydrate, fluoride, etc. as raw materials, there was prepared a material batch for a matrix glass so as to contain 47.8% by weight of CaO, 6.5% by weight of $P_2O_5$, 44.0% by weight of $SiO_2$, 1.5% by weight of MgO and 0.2% by weight of $F_2$. This batch was placed in a platinum crucible and melted for 2 hours at 1,550° C. The melt was poured into water and the resulting solid was dried. The dried solid was placed in a ball mill and ground to a particle size of 20 μm or below (625 meshes or finer). To the resulting glass powder was added a zirconia-alumina ceramic powder (average particle diameter: 0.3 μm) consisting of a partially stabilized zirconia (obtained according to the coprecipitation method and containing 3 mole % of $Y_2O_3$) and alpha-alumina, in a volume ratio of 20 (glass powder) : 80 (zirconia-alumina ceramic powder). They were wet-mixed in a ball mill for several hours and then dried. Thus, there were obtained various ceramic-glass mixed powders in which the weight ratio of the partially stabilized zirconia to the alpha-alumina was different. Each of these mixed powders was mixed with an organic binder and the resulting mixture was injection-molded into a cylindrical rod of 5 mm in diameter. The molding obtained was freed from the organic binder and then kept at 1,200° C. for 1 hour in an electric furnace, after which the molding was cooled to room temperature in the furnace to obtain a preliminary calcination product. The product was heated from room temerature to 1,250° C. at a constant temperature-elevating rate of 3° C./min while applying a pressure of 2,000 kg/cm² and then was kept at 1,250° C. for 2 hours, whereby hot isostatic pressing was conducted in a pressure medium gas atmosphere containing 5% by volume of oxygen. Thus, various zirconia-alumina ceramic/crystallized glass composites were obtained.

The section of each ceramic-crystallized glass composite was observed using a SEM. Each composite had substantially no pores, a dense structure and a relative density of at least 97% when measured according to the Archimedes method. The ceramic-crystallized glass composites were ground and, using the resulting powders, the crystalline phases precipitated in the matrix glass of each composite were identified according to the method of powder X-ray diffraction. In all the composites, crystals of apatite and wollastonite were precipitated in the respective glasses. Further, each composite was subjected to three-point bending test. The relationships between alpha-alumina content (wt. %) in zirconia-alumina ceramic and three-point bending strength, of the composites are shown in FIG. 1. As is clear from FIG. 1, the inorganic biomaterials of this Example in which the alpha-alumina content in zirconia-alumina ceramic varied from 0 to 99 wt. % showed far higher bending strengths (the highest value: 15,300 kg/cm²) than conventional inorganic biomaterials having bioactivity and had a color very close to that of living human bones.

EXAMPLE 3

(PRODUCTION OF ZIRCONIA CERAMIC/CRYSTALLIZED GLASS COMPOSITE BY USING HOT ISOSTATIC PRESSING IN OXYGEN ATMOSPHERE)

Using oxide, carbonate, phosphate, hydrate, fluoride, etc. as raw material, there was prepared a material batch for a matrix glass so as to contain 47.8% by weight of CaO, 6.5 by weight of $P_2O_5$, 44.0% by weight of $SiO_2$, 1.5% by weight of MgO and 0.2% by weight of $F_2$. This batch was placed in a platinum crucible and melted at 1,550° C. for 2 hours. The melt was poured into water. The resulting solid was dried and ground in a ball mill to a particle size of 20 μm or below (625 meshes or finer). To the resulting glass powder added a partialy stabilized zirconia ceramic powder (average particle diameter: 0.3 μm) obtained according to the coprecipitation method and containing 2.5 mole % of $Y_2O_3$, and they were wet-mixed in a ball mill for several hours and then dried. This ceramic-glass mixed powder was mixed with an organic binder, and the mixture was injection-molded into a cylindrical rod of 5 mm in diameter. The resulting molding was freed from the organic binder, after which the molding was kept at 650° to 1,500° C. for 1 hour in an electric furnace to increase the relative density to at least 90%. The molding was then cooled to room temperature in the furnace to obtain a preliminary calcination product. (In this Example, the cooling to room temperature was conducted for the convenience of the apparatus used. However, this cooling is not requisite, and the similar properties of the final product are obtained without cooling.) The preliminary calcination product was heated from room temperature to 1,200° C. at a constant temperature-elevating rate of 3° C./min while applying a pressure of 2,000 kg/cm² and thereafter was kept at 1,200° C. for 2 hours, whereby hot isostatic pressing was conducted in a pressure medium gas atmosphere containing 5% by volume of oxygen. Thus, various zirconia ceramic-crystallized glass composites were obtained.

Figure 2:
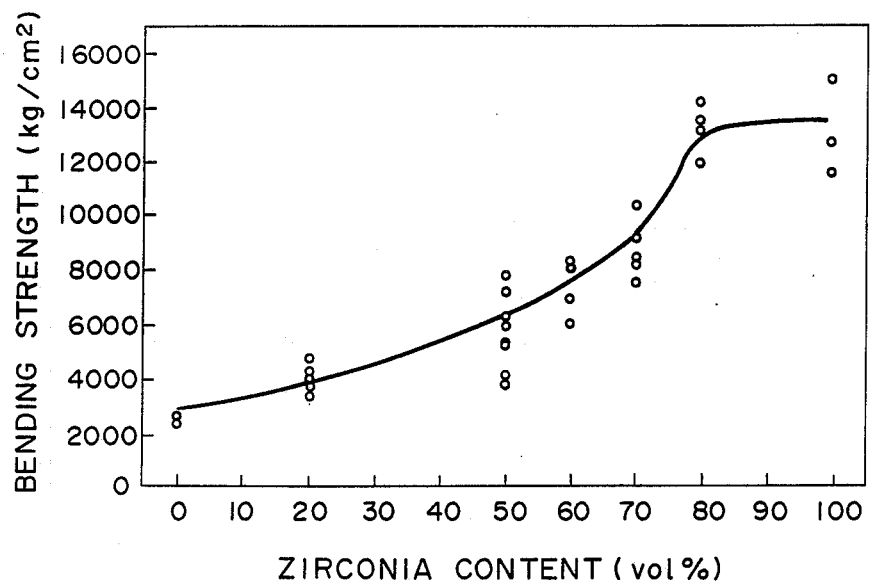
FIG. 2 is a graph showing the relationship between zirconia content (vol. %) and bending strength, of an inorganic biomaterial consisting of a zirconia ceramic/crystallized glass composite, obtained according to the present invention.

The section of each ceramic-crystallized glass composite was observed using a SEM. All the composites had substantially no pores, a dense structure and a relative density of at least 98% when measured according to the Archimedes method. These composites were ground and, using the powders obtained, the crystalline phases precipitated in the matrix glass of each composite were identified according to the method of powder X-ray diffraction. In all the composites, crystals of apatite and wollastonite were formed. Each composite was further subjected to three-point bending test. The relationship between zirconia content (vol. %) in composite and three-point bending strength of each composite is shown in FIG. 2. As is clear from FIG. 2, the bending strengths of the inorganic biomaterials of this Example each consisting of a zirconia ceramic-crystallized glass composite, increased with the increase of zirconia content in composite (the highest bending strength: 14,500 kg/cm²) and were far higher than the bending strengths of the conventional inorganic biomaterials having bioactivity. Moreover, each of the inorganic biomaterials obtained in this Example had a color very close to that of living human bones when visually compared with the bones.

EXAMPLE 4

(PRODUCTION OF ALUMINA CERAMIC/CRYSTALLIZED GLASS COMPOSITE BY USING HOT ISOSTATIC PRESSING IN OXYGEN ATMOSPHERE)

Using oxide, carbonate, phosphate, hydrate, fluoride, etc. as raw materials, there was prepared a material batch for a matrix glass so as to contain 47.8% by weight of CaO, 6.5% by weight of $P_2O_5$, 44.0% by weight of $SiO_2$, 1.5% by weight of MgO and 0.2% by weight of $F_2$. The batch was placed in a platinum crucible and melted at 1,550° C. for 2 hours. The resulting melt was poured into water. The solid obtained was dried and ground in a ball mill to a particle size of 20 μm or below (625 meshes or finer). To the resulting glass powder was added an alumina ceramic powder (average particle diameter: 1 μm, and they were wet-mixed in a ball mill for several hours and then dried. The resulting ceramic-glass mixed powder was mixed with an organic binder, and the mixture was injection-molded into a cylindrical rod of 5 mm in diameter. The molding obtained was freed from the organic binder and then was kept in an electric furnace at 650° to 1,500° C. for 1 hour to increase the relative density to at least 90%, after which it was cooled to room temperature in the furnace to obtain a preliminary calcination product. This product was heated from room temperature to 1,300° C. at a constant temperature-elevating rate of 3° C./min while applying a pressure of 2,000 kg/cm² and then was kept at 1,300° C. for 2 hours, whereby hot isostatic pressing was conducted in a pressure medium gas atmosphere containing 5% by volume of oxygen. Thus, various alumina ceramic-crystallized glass composites were produced.

Figure 3:
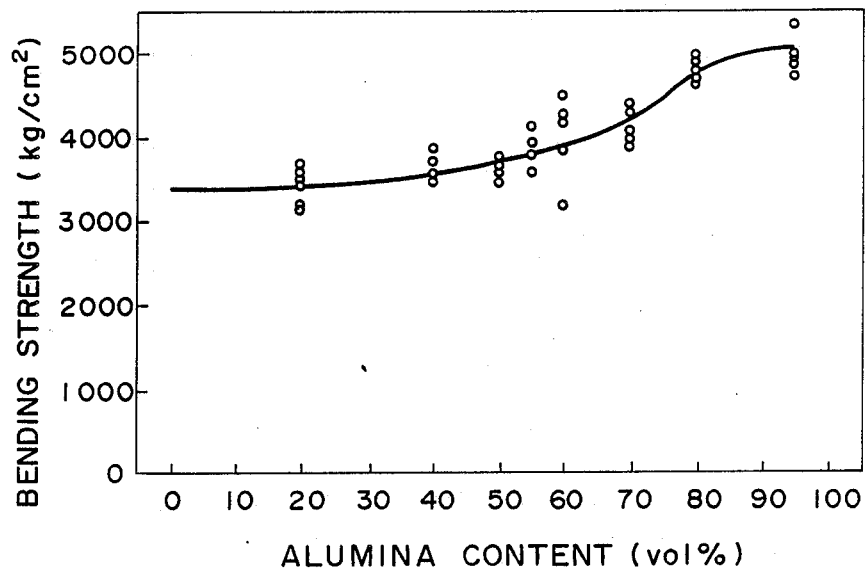
FIG. 3 is a graph showing the relationship between alumina content (vol. %) and bending strength, of an inorganic biomaterial of an alumina ceramic/crystallized glass composite, obtained according to the present invention.

These composites had relative density of 95-98% when measured according to the Archimedes method. The composites were ground and, using the powders obtained, the crystalline phases precipitated in the matrix glass of each composite were identified according to the method of powder X-ray diffraction. Crystals of apatite and wollastonite were precipitated in the glass, and any phase formed by the reaction of the glass and alumina was not found. Further, each composite was subjected to three-point bending test. The relationships between alumina content (vol. %) in composits and three-point bending strength are shown in FIG. 3. As is clear from FIG. 3, all of the inorganic biomaterials of this Example each consisting of an alumina ceramic-crystallized glass composite have high bending strengths ranging from 3,500 to 5,000 kg/cm² and possess a color very close to that of living human bones.

EXAMPLE 5

(PRODUCTION OF ZIRCONIC CERAMIC/CRYSTALLIZED GLASS COMPOSITE BY USING HOT ISOSTATIC PRESSING IN OXYGEN ATMOSPHERE)

Using oxide, carbonate, phosphate, hydrate, fluoride, etc. as raw material, there was prepared a material batch for a matrix glass having a composition as shown in Table 2. The batch was melted in a platinum crucible at 1,450° to 1,550° C. for 2 hours. The resulting melt was poured into water. The solid obtained was dried and ground in a ball mill to a particle size of 20μm or below (625 meshes or finer). To the resulting glass powder was added a partially stabilized zirconia powder (average particle diameter: 0.3 μm) obtained according to the coprecipitation method and containing 2.5 mole % of $Y_2O_3$, in a volume ratio of 80 (glass powder) : 20 (zirconia powder). They were wet-mixed in a ball mill for several hours and then dried. The resulting mixture of the ceramic powder and the glass powder was mixed with an organic binder and injection-molded to obtain a cylindrical rod of 5 mm in diameter. The molding was freed from the organic binder and then kept in an electric furnace for 1 hour at a temperature as shown in Table 2, after whcich it was cooled to room temperature in the furnace to obtain a preliminary calcination product. This product was heated from room temperature to a temperature as shown in Table 2, at a constant temperature-elevating rate of 3° C./min while applying a pressure of 2,000 kg/cm² and then was kept at a predetermined temperature for 2 hours, whereby hot isostatic pressing was conducted in a pressure medium gas atmosphere containing 5% by volume of oxygen. Thus, various zirconia ceramic-crystallized glass composites were produced.

These composits were measured for relative density according to the Archimedes method. They had relative densities of at least 98%. They were ground and, using the resulting powders, the crystalline phases precipitated in the matrix glass of each composite were identified according to the method of powder X-ray diffraction. The ceramic-crystallized glass composites were further subjected to three-point bending test. The three-point bending strength of each composite is shown in Table 2, together with the glass composition, the crystalline phases precipitated in the glass, the temperature of preliminary calcination, and the temperature of hot isostatic pressing. As is clear from Table 2, each of the inorganic biomaterials of this Example had a high bending strength ranging from 3,000 to 4,500 kg/cm$^2$ and a color very close to that of living human bones. Moreover, the inorganic biomaterials of this Example had very excellent biocompatibility without sacrificing the strength, since they were obtained from a mixture of a zirconia powder and a glass powder in which the glass powder (contributing to biocompatibility when crystallized) was more than the zirconia powder [80 (glass powder) : 20 (zirconia powder) by volume].

EXAMPLE 6
(PRODUCTION OF ZIRCONIA CERAMIC AND ALUMINA CERAMIC/CRYSTALLIZED GLASS COMPOSITE BY USING A POWDER MIXTURE OF ZIRCONIA CERAMIC AND ALUMINA CERAMIC AND HOT ISOSTATIC PRESSING IN OXYGEN ATMOSPHERE)

The procedures of Example 4 were repeated except that in place of alumina ceramic powder was used a 1/1 (v/v) mixture of alumina ceramic powder (average particle diameter: 1 μm) and partially stabilized zirconia powder (average particle diameter : 0.3 μm) obtained according to the coprecipitation method and containing 2.5 mole % of $Y_2O_3$, which ceramic mixture was then mixed with the previously obtained glass powder in a volume ratio of 40 (ceramic mixture) : 60 (glass powder), and thereafter the obtained molding was preliminarily calcinated at 800° to 1000° C. for 1 hour to increase the relative density to at least 90%.

The composite obtained after hot isostatic pressing in oxygen atmosphere had a relative density of 98% when measured according to the Archimedes method. The composite was ground and, using the powder obtained, the crystalline phases precipitated in the matrix glass were identified according to the method of poder X-ray diffraction. Crystals of apatite and wollastonite were precipitated in the glass, and any phase formed by the reaction of the glass and alumina was not found. Further, the composite was subjected to three-point bending test. The inorganic biomaterial of this Example consisting of zirconia ceramic and alumina ceramic/-crystallized glass composite had a high bending strength of 4500 kg/cm$^2$ and possess a color very close to that of living human bones.

TABLE 1

| | No. | 1 | 2 | 3 | 4 | 5 | 6 | 7 |
|---|---|---|---|---|---|---|---|---|
| Glass comp. (wt. %) | CaO | 47.5 | 49.2 | 23.2 | 55.6 | 44.7 | 36.3 | 26.8 |
| | $P_2O_5$ | 14.0 | 1.0 | 27.0 | 22.0 | 16.3 | 16.3 | 14.1 |
| | $SiO_2$ | 38.5 | 49.8 | 49.8 | 22.4 | 34.2 | 35.4 | 34.1 |
| | Others | | | | | MgO 4.6 $F_2$ 0.2 | MgO 11.5 $F_2$ 0.5 | MgO 11.5 $Al_2O_3$ 12.7 $F_2$ 0.8 |
| Comp. & Amt. added of $ZrO_2$—$Al_2O_3$ | tetragonal $ZrO_2$ (wt %) | 60 | 60 | 60 | 60 | 80 | 80 | 80 |
| | α—$Al_2O_3$ (wt %) | 40 | 40 | 40 | 40 | 20 | 20 | 20 |
| | Amt. (vol. %) | 20 | 20 | 20 | 20 | 20 | 20 | 20 |
| Crystalline phases precipitated in the matrix glass | | Apatite Wollastonite | Apatite Wollastonite | Apatite Wollastonite β-TCP* | Apatite Wollastonite | Apatite Wollastonite Diopside | Apatite Diopside | Apatite Anorthite Diopside Forsterite β-TCP |
| Bending strength (kg/cm$^2$) | | 2800 | 3200 | 2900 | 2800 | 3000 | 3000 | 3100 |
| | No. | 8 | 9 | 10 | 11 | 12 | 13 | 14 |
| Glass comp. (wt. %) | CaO | 24.6 | 26.1 | 16.6 | 47.4 | 47.4 | 48.3 | 47.9 |
| | $P_2O_5$ | 16.0 | 23.0 | 16.2 | 6.2 | 6.2 | 6.3 | 6.3 |
| | $SiO_2$ | 28.7 | 29.8 | 37.2 | 42.2 | 42.2 | 43.2 | 42.6 |
| | Others | MgO 30.7 | MgO 18.6 $F_2$ 0.5 $Li_2O$ 2.0 | MgO 29.5 $F_2$ 0.5 | $Y_2O_3$ 2.0 $ZrO_2$ 2.0 $F_2$ 0.2 | MgO 2.0 $Ta_2O_5$ 2.0 $F_2$ 0.2 | $F_2$ 0.2 $TiO_2$ 2.0 | $F_2$ 0.2 $K_2O$ 3.0 |
| Comp. & Amt. added of $ZrO_2$—$Al_2O_3$ ceramic | tetragonal $ZrO_2$ (wt %) | 80 | 80 | 80 | 80 | 80 | 80 | 80 |
| | α—$Al_2O_3$ (wt %) | 20 | 20 | 20 | 20 | 20 | 20 | 20 |
| | Amt. (vol. %) | 20 | 20 | 20 | 20 | 20 | 20 | 20 |
| Crystalline phases precipitated in the matrix glass | | Apatite Forsterite Diopside β-TCP | Apatite Akermanite Diopside β-TCP | Apatite Diopside Forsterite | Apatite Wollastonite | Apatite Wollastonite | Apatite Wollastonite | Apatite Wollastonite |
| Bending strength (kg/cm$^2$) | | 3200 | 3000 | 3200 | 3000 | 3000 | 3000 | 3000 |
| | No. | 15 | 16 | 17 | 18 | 19 | 20 | |

TABLE 1-continued

| | | | | | | | |
|---|---|---|---|---|---|---|---|
| Glass comp. (wt. %) | CaO | 48.3 | 48.3 | 48.3 | 48.3 | 49.3 | 47.8 |
| | P$_2$O$_5$ | 6.3 | 6.3 | 6.3 | 6.3 | 6.5 | 6.5 |
| | SiO$_2$ | 43.2 | 43.2 | 43.2 | 43.2 | 44.0 | 44.0 |
| | others | F$_2$ 0.2 | F$_2$ 0.2 | F$_2$ 0.2 | F$_2$ 0.2 | F$_2$ 0.2 | MgO 1.5 |
| | | SrO 2.0 | Nb$_2$O$_5$ 2.0 | Na$_2$O 2.0 | B$_2$O$_3$ 2.0 | | F$_2$ 0.2 |
| Comp. & Amt. added of ZrO$_2$—Al$_2$O$_3$ | tetragonal ZrO$_2$ (wt %) | 80 | 80 | 80 | 80 | 60 | 60 |
| | α—Al$_2$O$_3$ (wt %) | 20 | 20 | 20 | 20 | 40 | 40 |
| | Amt. (vol. %) | 20 | 20 | 20 | 20 | 20 | 10 |
| Crystalline phases precipitated in the matrix glass | | Apatite Wollastonite | Apatite Wollastonite | Apatite Wollastonite | Apatite Wollastoonite | Apatite Wollastonite | Apatite Wollastonite |
| Bending strength (kg/cm$^2$) | | 3000 | 2800 | 2800 | 3000 | 3100 | 3000 |

| No. | | 21 | 22 | 23 | 24 | 25 | 26 |
|---|---|---|---|---|---|---|---|
| Glass comp. (wt. %) | CaO | 47.8 | 47.8 | 47.8 | 47.8 | 47.8 | 47.8 |
| | P$_2$O$_5$ | 6.5 | 6.5 | 6.5 | 6.5 | 6.5 | 6.5 |
| | SiO$_2$ | 44.0 | 44.0 | 44.0 | 44.0 | 44.0 | 44.0 |
| | Others | MgO 1.5 | MgO 1.5 | MgO 1.5 | MgO 1.5 | MgO 1.5 | MgO 1.5 |
| | | F$_2$ 0.2 | F$_2$ 0.2 | F$_2$ 0.2 | F$_2$ 0.2 | F$_2$ 0.2 | F$_2$ 0.2 |
| Comp. & Amt. ZrO$_2$—Al$_2$O$_3$ | tetragonal | 60 | 60 | 60 | 60 | 90 | 40 |
| | α—Al$_2$O$_3$ (wt %) | 40 | 40 | 40 | 40 | 10 | 60 |
| | Amt. (vol. %) | 20 | 30 | 40 | 50 | 20 | 20 |
| Crystalline phases precipitated in the matrix glass | | Apatite Wollastonite | Apatite Wollastonite | Apatite Wollastonite | Apatite Wollastonite | Apatite Wollastonite | Apatite Wollastonite |
| Bending strength (kg/cm$^2$) | | 3500 | 3800 | 3800 | 3700 | 3800 | 3400 |

| No. | | 27 | 28 | 29 | 30 | 31 | 32 |
|---|---|---|---|---|---|---|---|
| Glass comp. (wt. %) | CaO | 47.8 | 47.8 | 12.0 | 45.0 | 45.0 | 45.0 |
| | P$_2$O$_5$ | 6.5 | 6.5 | 15.5 | 6.0 | 6.0 | 6.0 |
| | SiO$_2$ | 44.0 | 44.6 | 47.7 | 39.0 | 39.0 | 39.0 |
| | Others | MgO 1.5 | MgO 1.5 | Al$_2$O$_3$ 24.8 | K$_2$O 9.5 | Li$_2$O 9.5 | Na$_2$O 9.5 |
| | | F$_2$ 0.2 | F$_2$ 0.2 | | F$_2$ 0.5 | F$_2$ 0.5 | F$_2$ 0.5 |
| Comp. & Amt. added of ZrO$_2$—Al$_2$O$_3$ | tetragonal ZrO$_2$ (wt %) | 20 | 10 | 80 | 80 | 80 | 80 |
| | α—Al$_2$O$_3$ (wt %) | 80 | 90 | 20 | 20 | 20 | 20 |
| | Amt. (vol. %) | 20 | 20 | 20 | 20 | 20 | 20 |
| Crystalline phases precipitated in the matrix glass | | Apatite Wollastonite | Apatite Wollastonite | Apatite Wollastonite β-TCP | Apatite Wollastonite β-TCP | Apatie Wollastonite β-TCP | Apatite Wollastonite β-TCP |
| Bending strength (kg/cm$^2$) | | 3300 | 3100 | 3000 | 2800 | 2800 | 2800 |

| No. | | 33 | 34 | 35 | 36 | 37 | 38 |
|---|---|---|---|---|---|---|---|
| Glass comp. (wt. %) | CaO | 45.0 | 45.0 | 45.0 | 45.0 | 45.0 | 45.0 |
| | P$_2$O$_5$ | 6.0 | 6.0 | 6.0 | 6.0 | 6.0 | 6.0 |
| | SiO$_2$ | 39.0 | 39.0 | 39.0 | 39.0 | 39.0 | 39.0 |
| | Others | TiO$_2$ 9.5 | ZrO$_2$ 9.5 | SrO 9.5 | Nb$_2$O$_5$ 9.5 | Ta$_2$O$_5$ 9.5 | B$_2$O$_3$ 9.5 |
| | | F$_2$ 0.5 | F$_2$ 0.5 | F$_2$ 0.5 | F$_2$ 0.5 | F$_2$ 0.5 | F$_2$ 0.5 |
| Comp. & Amt. added of ZrO$_2$—Al$_2$O$_3$ | tetragonal ZrO$_2$ (wt %) | 80 | 80 | 80 | 80 | 80 | 80 |
| | α—Al$_2$O$_3$ (wt %) | 20 | 20 | 20 | 20 | 20 | 20 |
| | Amt. (vol. %) | 20 | 20 | 20 | 20 | 20 | 20 |
| Crystalline phases precipitated in the matrix glass | | Apatite Wollastonite β-TCP | Apatite Wollastonite β-TCP | Apatite Wollastonite β-TCP | Apatite Wollastonite β-TCP | Apatite Wollastonite β-TCP | Apatite Wollastonite β-TCP |
| Bending strength (kg/cm$^2$) | | 3000 | 3200 | 2900 | 2800 | 2800 | 2800 |

| No. | | 39 | 40 | 41 | 42 | 43 | 44 |
|---|---|---|---|---|---|---|---|
| Glass comp. (wt. %) | CaO | 45.0 | 45.0 | 47.8 | 47.8 | 47.8 | 47.8 |
| | P$_2$O$_5$ | 6.0 | 6.0 | 6.5 | 6.5 | 6.5 | 6.5 |
| | SiO$_2$ | 44.5 | 44.0 | 44.0 | 44.0 | 44.0 | 44.0 |
| | Others | F$_2$ 4.5 | Y$_2$O$_3$ 5.0 | MgO 1.5 | MgO 1.5 | MgO 1.5 | MgO 1.5 |
| | | | | F$_2$ 0.2 | F$_2$ 0.2 | F$_2$ 0.2 | F$_2$ 0.2 |
| Comp. & Amt. added of ZrO$_2$—Al$_2$O$_3$ | tetragonal ZrO$_2$ (wt %) | 80 | 80 | 99.7 | 99.5 | 99 | 95 |
| | α—Al$_2$O$_3$ (wt %) | 20 | 20 | 0.3 | 0.5 | 1 | 5 |
| | Amt. (vol. %) | 20 | 20 | 20 | 20 | 20 | 20 |
| Crystalline phases precipitated in the matrix glass. | | Apatite Wollastonite | Apatite Wollastonite | Apatite Wollastonite | Apatite Wollastonite | Apatite Wollastonite | Apatite Wollastonite |
| Bending Strength (kg/cm$^2$) | | 2800 | 3200 | 3800 | 3500 | 3800 | 3700 |

*β-TCP = Tricalcium phosphate of beta type

TABLE 2

| No. | 1** | 2** | 3** | 4 | 5 |
|---|---|---|---|---|---|
| Glass comp. (wt. %) CaO | 47.8 | 47.8 | 47.8 | 47.8 | 47.8 |
| $P_2O_5$ | 6.5 | 6.5 | 6.5 | 6.5 | 6.5 |
| $SiO_2$ | 44.0 | 44.0 | 44.0 | 44.0 | 44.0 |
| Others | MgO 1.5 $F_2$ 0.2 | MgO 1.5 $F_2$ 0.2 | MgO 1.5 $F_2$ 0.2 | MgO 1.5 $F_2$ 0.2 | MgO 1.5 $F_2$ 0.2 |
| Crystalline phases precipitated in the matrix glass | Apatite Wollastonite | Apatite Wollastonite | Apatite Wollastonite | Apatite Wollastonite | Apatite Wollastonite |
| Temp. of pre-calcination (°C.) | 500 | 700 | 900 | 700 | 900 |
| Temp. of hot isostatic pressing (°C.) | 800 | 800 | 800 | 1200 | 1200 |
| Bending strength (kg/cm²) | 500 | 500 | 800 | 3500 | 4500 |

| No. | 6 | 7 | 8 | 9 | 10 |
|---|---|---|---|---|---|
| Glass comp. (wt. %) CaO | 47.8 | 47.8 | 47.8 | 47.8 | 47.8 |
| $P_2O_5$ | 6.5 | 6.5 | 6.5 | 6.5 | 6.5 |
| $SiO_2$ | 44.0 | 44.0 | 44.0 | 44.0 | 44.0 |
| Others | MgO 1.5 $F_2$ 0.2 | MgO 1.5 $F_2$ 0.2 | MgO 1.5 $F_2$ 0.2 | MgO 1.5 $F_2$ 0.2 | MgO 1.5 $F_2$ 0.2 |
| Crystalline phases precipitated in the matrix glass | Apatite Wollastonite | Apatite Wollastonite | Apatite Wollastonite | Apatite Wollastonite | Apatite Wollastonite |
| Temp. of pre-calcination (°C.) | 1100 | 1300 | 1500 | 900 | 900 |
| Temp. of hot isostatic pressing (°C.) | 1200 | 1200 | 1200 | 900 | 1000 |
| Bending strength (kg/cm²) | 3300 | 3000 | 3000 | 2900 | 3000 |

| No. | 11 | 12 | 13 | 14 | 15 |
|---|---|---|---|---|---|
| Glass comp. (wt. %) CaO | 47.8 | 47.8 | 47.8 | 47.5 | 49.2 |
| $P_2O_5$ | 6.5 | 6.5 | 6.5 | 14.0 | 1.0 |
| $SiO_2$ | 44.0 | 44.0 | 44.0 | 38.5 | 49.8 |
| Others | MgO 1.5 $F_2$ 0.2 | MgO 1.5 $F_2$ 0.2 | MgO 1.5 $F_2$ 0.2 | | |
| Crystalline phases precipitated in the matrix glass | Apatite Wollastonite | Apatite Wollastonite | Apatite Wollastonite | Apatite Wollastonite | Apatite Wollastonite |
| Temp. of pre-calcination (°C.) | 900 | 900 | 900 | 900 | 900 |
| Temp. of hot isostatic pressing (°C.) | 1100 | 1300 | 1500 | 1200 | 1200 |
| Bending strength (kg/cm²) | 4000 | 3500 | 3000 | 3000 | 3500 |

| No. | 16 | 17 | 18 | 19 | 20 |
|---|---|---|---|---|---|
| Glass comp. (wt. %) CaO | 23.2 | 55.6 | 44.7 | 36.3 | 26.8 |
| $P_2O_5$ | 27.0 | 22.0 | 16.3 | 16.3 | 14.1 |
| $SiO_2$ | 49.8 | 22.4 | 34.2 | 35.4 | 34.1 |
| Others | | | MgO 1.5 $F_2$ 0.2 | MgO 1.5 $F_2$ 0.2 | MgO 1.5 $F_2$ 0.2 |
| Crystalline phases precipitated in the matrix glass | Apatite Wollastonite | Apatite Wollastonite | Apatite Wollastonite | Apatite Wollastonite | Apatite Wollastonite |
| Temp. of pre-calcination (°C.) | 900 | 900 | 900 | 900 | 900 |
| Temp. of hot isostatic pressing (°C.) | 1200 | 1200 | 1200 | 1200 | 1200 |
| Bending strength (kg/cm²) | 3000 | 3250 | 3250 | 3750 | 4000 |

| No. | 6 | 7 | 8 | 9 | 10 |
|---|---|---|---|---|---|
| Glass comp. (wt. %) CaO | 47.8 | 47.8 | 47.8 | 47.8 | 47.8 |
| $P_2O_5$ | 6.5 | 6.5 | 6.5 | 6.5 | 6.5 |
| $SiO_2$ | 44.0 | 44.0 | 44.0 | 44.0 | 44.0 |
| Others | MgO 1.5 $F_2$ 0.2 | MgO 1.5 $F_2$ 0.2 | MgO 1.5 $F_2$ 0.2 | MgO 1.5 $F_2$ 0.2 | MgO 1.5 $F_2$ 0.2 |
| Crystalline phases precipitated in the matrix glass | Apatite Wollastonite | Apatite Wollastonite | Apatite Wollastonite | Apatite Wollastonite | Apatite Wollastonite |
| Temp. of pre-calcination (°C.) | 1100 | 1300 | 1500 | 900 | 900 |
| Temp. of hot isostatic pressing (°C.) | 1200 | 1200 | 1200 | 900 | 1000 |
| Bending strength (kg/cm²) | 3300 | 3000 | 3000 | 2900 | 3000 |

| No. | 21 | 22 | 23 | 24 | 25 | 26 |
|---|---|---|---|---|---|---|
| Glass comp. (wt. %) CaO | 24.6 | 26.1 | 16.6 | 47.4 | 47.4 | 48.3 |
| $P_2O_5$ | 16.0 | 23.0 | 16.2 | 6.2 | 6.2 | 6.3 |
| $SiO_2$ | 28.7 | 29.8 | 37.2 | 42.2 | 42.2 | 43.2 |
| Others | MgO 30.7 | MgO 18.6 $F_2$ 0.5 $Li_2O$ 2.0 | MgO 29.5 $F_2$ 0.5 | $Y_2O_3$ 2.0 $ZrO_2$ 2.0 $F_2$ 0.2 | MgO 2.0 $Ta_2O_5$ 2.0 $F_2$ 0.2 | $F_2$ 0.2 $TiO_2$ 2.0 |
| Crystalline phases precipitated in the matrix glass | Apatite Fosterite Diopside β-TCP | Apatite Akermanite Diopside β-TCP | Apatite Diopside | Apatite Wollastonite Fosterite | Apatite Wollastonite | Apatite |
| Temp. of pre-calcination (°C.) | 900 | 900 | 900 | 900 | 900 | 900 |

TABLE 2-continued

| | | | | | | |
|---|---|---|---|---|---|---|
| Temp. of hot isostatic pressing (°C.) | 1200 | 1200 | 1200 | 1200 | 1200 | 1200 |
| Bending strength (kg/cm$^2$) | 3750 | 3750 | 4000 | 4100 | 4000 | 3750 |

| | No. | 27 | 28 | 29 | 30 | 31 |
|---|---|---|---|---|---|---|
| Glass comp. (wt. %) | CaO | 47.9 | 48.3 | 48.3 | 48.3 | 48.3 |
| | P$_2$O$_5$ | 6.3 | 6.3 | 6.3 | 6.3 | 6.3 |
| | SiO$_2$ | 42.6 | 43.2 | 43.2 | 43.2 | 43.2 |
| | Others | F$_2$ 0.2 K$_2$O 3.0 | F$_2$ 0.2 SrO 2.0 | F$_2$ 0.2 Nb$_2$O$_5$ 2.0 | F$_2$ 0.2 Na$_2$O 2.0 | F$_2$ 0.2 B$_2$O$_3$ 2.0 |
| Crystalline phases precipitated in the matrix glass | | Apatite Wollastonite | Apatite Wollastonite | Apatite Wollastonite | Apatite Wollastonite | Apatite Wollastonite |
| Temp. of pre-calcination (°C.) | | 900 | 900 | 900 | 900 | 900 |
| Temp. of hot isostatic pressing (°C.) | | 1200 | 1200 | 1200 | 1200 | 1200 |
| Bending strength (kg/cm$^2$) | | 3250 | 3750 | 4000 | 3750 | 3000 |

| | No. | 32 | 33 | 34 | 35 | 36 |
|---|---|---|---|---|---|---|
| Glass comp. (wt. %) | CaO | 49.3 | 12.0 | 45.0 | 45.0 | 45.0 |
| | P$_2$O$_5$ | 6.5 | 15.5 | 6.0 | 6.0 | 6.0 |
| | SiO$_2$ | 44.0 | 47.7 | 39.0 | 39.0 | 39.0 |
| | Others | F$_2$ 0.2 | Al$_2$O$_3$ 24.8 | K$_2$O 9.5 F$_2$ 0.5 | Li$_2$O 9.5 F$_2$ 0.5 | Na$_2$O 9.5 F$_2$ 0.5 |
| Crystalline phases precipitated in the matrix glass | | Apatite Wollastonite | Apatite Anorthite | Apatite Wollastonite | Apatite Wollastonite | Apatite Wollastonite |
| Temp. of pre-calcination (°C.) | | 900 | 900 | 900 | 900 | 900 |
| Temp. of hot isostatic pressing (°C.) | | 1200 | 1200 | 1200 | 1200 | 1200 |
| Bending strength (kg/cm$^2$) | | 4200 | 4400 | 3750 | 3750 | 3750 |

| | No. | 37 | 38 | 39 | 40 | 41 |
|---|---|---|---|---|---|---|
| Glass comp. (wt. %) | CaO | 45.0 | 45.0 | 45.0 | 45.0 | 45.0 |
| | P$_2$O$_5$ | 6.0 | 6.0 | 6.0 | 6.0 | 6.0 |
| | SiO$_2$ | 39.0 | 39.0 | 39.0 | 39.0 | 39.0 |
| | Others | TiO$_2$ 9.5 F$_2$ 0.5 | ZrO$_2$ 9.5 F$_2$ 0.5 | SrO 9.5 F$_2$ 0.5 | Nb$_2$O$_5$ 9.5 F$_2$ 0.5 | Ta$_2$O$_5$ 9.5 F$_2$ 0.5 |
| Crystalline phases precipitated in the matrix glass | | Apatite Wollastonite β-TCP | Apatite Wollastonite β-TCP | Apatite Wollastonite β-TCP | Apatite Wollastonite β-TCP | Apatite Wollastonite β-TCP |
| Temp. of pre-calcination | | 900 | 900 | 900 | 900 | 900 |
| Temp. of hot isostatic pressing (°C.) | | 1200 | 1200 | 1200 | 1200 | 1200 |
| Bending strength (kg/cm$^2$) | | 3750 | 4000 | 4200 | 4200 | 4100 |

| | No. | 42 | 43 | 44 |
|---|---|---|---|---|
| Glass comp. (wt. %) | CaO | 45.0 | 45.0 | 45.0 |
| | P$_2$O$_5$ | 6.0 | 6.0 | 6.0 |
| | SiO$_2$ | 39.0 | 44.5 | 44.0 |
| | Others | B$_2$O$_3$ 9.5 F$_2$ 0.5 | F$_2$ 4.5 | Y$_2$O$_3$ 5.0 |
| Crystalline phases precipitated in the matrix glass | | Apatite Wollastonite β-TCP | Apatite Wollastonite | Apatite Wollastonite |
| Temp. of pre-calcination | | 900 | 900 | 900 |
| Temp. of hot isotatic pressing (°C.) | | 1200 | 1200 | 1200 |
| Bending strength (kg/cm$^2$) | | 4000 | 4300 | 4300 |

**In Nos. 1, 2 and 3, either or both of the temperature of preliminary calcination and the temperature of hot isotatic pressing are out of the ranges specified in the present invention. Accordingly, Nos. 1, 2 and 3 are Comparative Examples.

What is claimed is:

1. An inorganic biomaterial comprising a ceramic-crystallized glass composite wherein a zirconia-alumina ceramic, in a weight ratio of zirconia to alumina in the range from 99.7:0.3 to 10:90, is dispersed in a crystallized glass consisting essentially of the following components in the following proportions:

| | |
|---|---|
| CaO | 12 to 56% by weight |
| P$_2$O$_5$ | 1 to 27% by weight |
| SiO$_2$ | 22 to 50% by weight |
| MgO | 0 to 34% by weight |
| Al$_2$O$_3$ | 0 to 25% by weight | in a total amount of at least 90% by weight, and the volume ratio of the crystallized glass to the zirconia-alumina ceramic is in a range from 5:95 to 95:5.

2. An inorganic biomaterial according to claim 1, wherein the crystallized glass further contains:
 (a) up to 10% by weight of at least one of K$_2$O, Li$_2$O, Na$_2$O, TiO$_2$, ZrO$_2$, SrO, Nb$_2$O$_5$, Ta$_2$O$_5$ and B$_2$O$_3$;
 (b) a up to 5% by weight of F$_2$ or Y$_2$O$_3$; or
 (c) both (a) and (b), provided the total amount of (a), (b) or (c) is not greater than 10% by weight.

* * * * *